United States Patent [19]

Kim

[11] 4,071,513
[45] Jan. 31, 1978

[54] SUBSTITUTED AZETIDINONE ALDEHYDES

[75] Inventor: Choung Un Kim, North Syracuse, N.Y.

[73] Assignee: Bristol-Myers Company, New York, N.Y.

[21] Appl. No.: 728,697

[22] Filed: Oct. 1, 1976

[51] Int. Cl.$^2$ ............................................. C07D 205/08
[52] U.S. Cl. .............................. 260/239 A; 260/307 F; 544/90
[58] Field of Search .................................... 260/239 A

[56] References Cited

U.S. PATENT DOCUMENTS 3,948,927   4/1976   Wolfe ............................... 260/239 A

OTHER PUBLICATIONS

S. Wolfe et al., CAN J. Chem. 52, 3996 (1974).
Derwent Farmdoc No. D0109X, 38606V and 38607V.
Cama et al., J. Amer. Chem. Soc., 96, 7582 (1974).
D. O. Spry, Tetrahedron Letters, 1972, p. 3717.
S. Kukolja, J. Amer. Chem. Soc., 93, 6267 (1971).

D. F. Corbeltt, J. Chem. Soc. Perkin I 185, (1974) and 432 (1975).
R. F. Borch et al., J. Amer. Chem. Soc., 93, 2897 (1971).

*Primary Examiner*—Alton D. Rollins
*Assistant Examiner*—Mark L. Berch
*Attorney, Agent, or Firm*—Herbert W. Taylor, Jr.

[57] ABSTRACT

Chemical transformation of the dihydrothiazine ring of a cephalosporin into the dihydrooxazine ring (1-oxacephem) was accomplished utilizing the novel intermediate having the structure

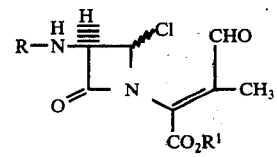

wherein R is an amino-protecting group and $R^1$ is the residue of an ester group which can be removed readily without disrupting the remainder of the molecule as illustrated by phenoxyacetyl as R and benzhydryl as $R^1$.

2 Claims, No Drawings

SUBSTITUTED AZETIDINONE ALDEHYDES

BACKGROUND OF THE INVENTION

1. Field of the Invention

The processes of the present invention produce compounds both old and new which are intermediates in the syntheses of β-lactam compounds.

2. Description of the Prior Art

Chemical transformations involving primarily monocyclic β-lactams have been reviewed in U.S. Pat. No. 3,948,927 (see columns 1 and 2) and disclosed therein and, for example, in U.S. Pat. Nos. 3,681,380; 3,843,682; 3,860,577; 3,862,164; 3,872,086; 3,880,872; 3,880,880; 3,883,517; 3,900,487; 3,917,644; 3,919,209; 3,920,696; 3,923,795; 3,925,363; 3,927,013; 3,939,151; 3,939,157; 3,943,123; 3,944,545; 3,951,951; 3,953,424; 3,954,732; and 3,960,851.

Excellent reviews are provided in the appropriate chapters of Cephalosporins and Penicillins – Chemistry and Biology, edited by Edwin H. Flynn, Academic Press, New York, 1972, e.g. Chapters 5 and 6.

A more recent review is A. K. Mukerjee and A. K. Singh, Reactions of Natural and Synthetic β-Lactams, Synthesis (International Journal of Methods in Synthetic Organic Chemistry) Number 9, 547–589 (September, 1975), Academic Press, New York.

SUMMARY OF THE INVENTION

There is provided by the present invention a compound having the formula

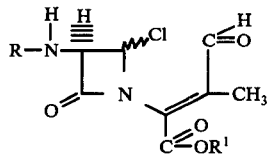

wherein R is an amine protecting group and $R^1$ is the residue of an ester group which can be removed readily including the individual isomers represented by the structures

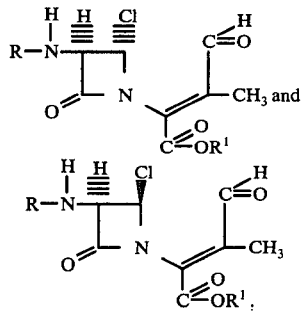

A preferred embodiment of the present invention is a compound having the formula

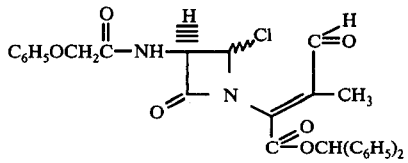

including the individual isomers represented by the structures

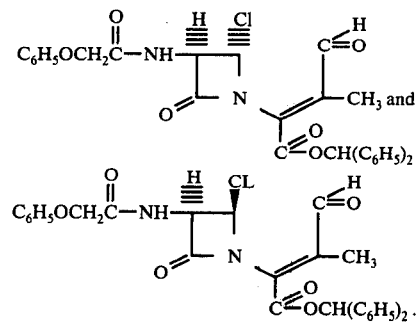

The generic structure can also be written in more detail as

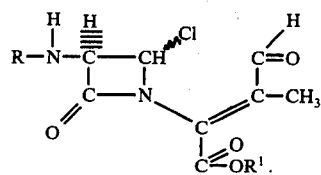

the amino protecting group R includes those conventional in the β-lactam art, particularly acyl, and includes but is not limited to, those named in the art as in U.S. Pat. Nos. 3,947,413; 3,932,465; 3,954,732; 3,660,396; and 3,948,927.

The carboxyl protecting group $R^1$ includes those conventional in the β-lactam art, and particularly those which are readily removed with disrupting a cepham ring when such is present, and includes but is not limited to those named in the art as in U.S. Pat. Nos. 3,947,413; 3,932,465; 3,954,732; and 3,660,396.

Derivatives of the type E (S. Wolfe et al., Can. J. Chem. 52, 3996 (1974); Belgium Pat. No. 832,174 (Derwent 00109X), ex. I-F, III-D, VI, XIII-C, claims 30–33) and F. (S. Wolfe et al., loc. cit.; Belgium Pat. No. 832,174, ex. II-C, VI, IX, claims 30, 31, 33) are known and have been shown to be convertible to 1-oxacephem (S. Wolfe et al., loc. cit.; Belgium Pat No. 832,174, ex. I-G, VII, claims 1, 3, 5–9) and epi-1-oxacephem (S. Wolfe et al., loc. cit.; Belgium Pat. No. 832,174, ex. I-G, II-H, III-E, claims 1, 2) derivatives. Various 1oxacephem derivatives have been shown to be interesting antibacterial agents [L. D. Cama and B. G. Christensen, J. Amer. Chem. Soc., 96, 7582 (1974)].

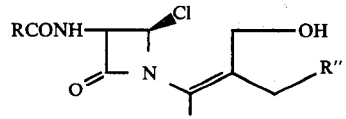

E

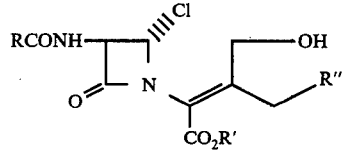

F

This invention discloses the preparation of derivatives of the type E and F in relatively few steps (compared to previously described methods) from relatively available cephem derivatives. Recent interest in the nuclear modified cephalosporins [1a, L. D. Cama and B. G. Christensen, J. Amer. Chem. Soc., 96, 7582 (1974); 1b, S. Wolfe, J. B. Ducep, K. C. Tin and S. L. Lee, Can. J. Chem. 52, 3996 (1974); 1c, West Germany Offenlegungsschrift No. 23 55 209 and 23 55 210 (Derwent abstracts 38606V and 38607V)], prompted me to attempt the chemical transformation of the dihydrothiazine ring of a cephalosporin 1 into the dihydrooxazine ring (1-oxacephem)[1a] 2.

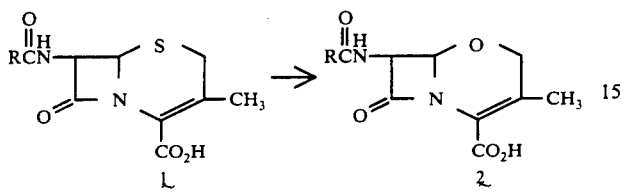

The reaction of the cephalosporin ester 3 with N-chlorosuccinimide in methanol-methylene chloride (1:1) gave the 2-methoxy cephem 4, [D. O. Spry, Tetrahedron Letters, 3717 (1972)] m.p. 132°–133° C. in 85% yield after recrystallization from ether. Treatment of 4 with chlorine in carbon tetrachloride (2.5 eq, −20° C., 60 min.) [S. Kukolja, J. Amer. Chem. Soc., 93, 6267 (1971)], followed by an aqueous work-up gave a quantitative conversion to the aldehyde 5 as a mixture of cis and trans isomers ($\alpha$ chloro/$\beta$ chloro $\simeq$ 1/9).

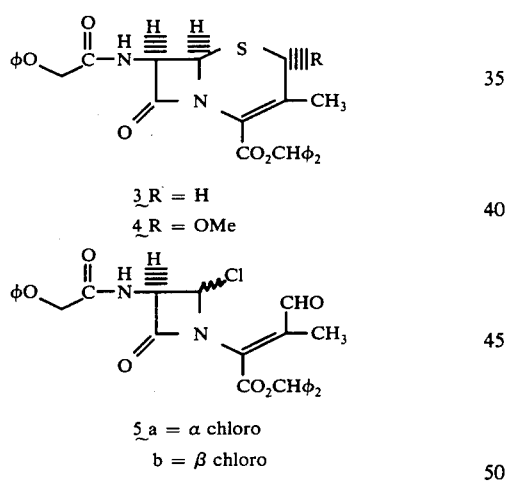

3 R = H
4 R = OMe 5 a = $\alpha$ chloro
  b = $\beta$ chloro

The chlorinolysis may proceed via intermediates 6 and 7 as shown in Scheme I. Intermediate 7 could be isolated by anhydrous work-up and quantitatively converted into the aldehyde 5 by water. It is not clear at this moment why the thermodynamically less stable $\beta$-chloro isomer 5b is predominant in the reaction mixture.

Scheme I

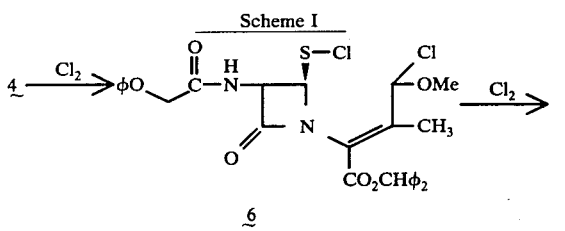

6

-continued
Scheme I

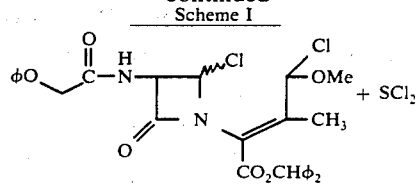

7

The reaction of the isomeric mixture 5 with $AgBF_4$-$Ag_2O$ (1:1) in methylene chloride gave the oxazolone 8 in 85% yield. Treatment of a methylene chloride solution of 8 with HCl gas at 0° C. gave quantitatively the $\alpha$-chloro isomer 5a by a stereospecific ring opening [D. F. Cobett and R. J. Stoodley, J. Chem. Soc., Perkin I 185 (1974); ibid., 432 (1975)].

Reduction of aldehyde 5 with sodium cyanoborohydride [R. F. Borch, M.D. Bernstein and H. D. Durst, J. Amer. Chem. Soc., 93, 2897 (1971)], in THF-acetic acid produced the alcohol 9 in over 90% yield. Ring closure of 9a or a mixture of 9a and 9b with $AgBF_4$-$Ag_2O$ (1:1) in methylene chloride gave the 6-epi-1-oxacephem 10b in 87% yield after silica gel chromatography.

Hydrogenation of 10b over Pd/C in dioxane-water gave the free acid 12b, m.p. 139°–141° C. which displayed no antibacterial activity when compared with 1 (R = $\phi OCH_2$) at levels as high as 125 mcg./ml.

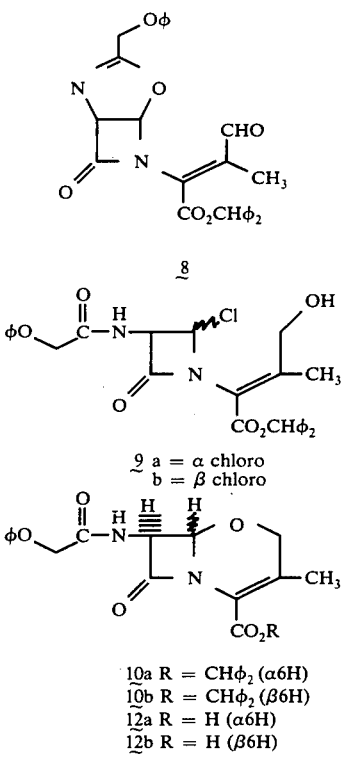

8

9 a = $\alpha$ chloro
  b = $\beta$ chloro

10a R = $CH\phi_2$ ($\alpha$6H)
10b R = $CH\phi_2$ ($\beta$6H)
12a R = H ($\alpha$6H)
12b R = H ($\beta$6H)

Chemical Shift Values $(CDCl_3)^{a,b}$

| Compounds | $\delta H6$ | $\delta H7$ |
|---|---|---|
| 4 | 5.1 (d, J=g.0) | 5.9 (q, J=5.0, 9.8) |
| 5a | 6.2 (d, J=1.2) | 5.1 (q, J=1.2, 10) |
| 5b | 6.3 (d, J=4.2) | 5.7 (q, J=4.2, 11.5) |
| 8 | 6.3 (d, J=4.5) | 5.4 (d, J=4.5) |
| 9b | 5.9 (d, J=3.9) | 5.6 (q, J=3.9, 9.5) |

-continued

Chemical Shift Values (CDCl₃)[a][b]

| Compounds | δH6 | δH7 |
|---|---|---|
| 10b | 5.2 (d, J=0.8) | 4.8 (q, J=0.8, 8.7) |
| 12b | 5.1 (d, J=0.8) | 4.7 (q, J=0.8, 8.5) |

[a]Varian HA 100 MHz spectrometer
[b]J values in hertz
Satisfactory elemental analyses were obtained for all compounds.

DESCRIPTION OF THE PREFERRED EMBODIMENTS

EXAMPLE 1

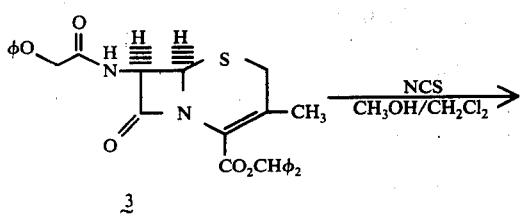

To a stirred solution of 514 mg. (1.0 mmole) of the cephem benzhydryl ester 3 in 30 ml. of methanolmethylene chloride (1:1) was added 147 mg. (1.1 mmole) of N-chlorosuccinimide (NCS) and the solution was stirred for 3 hours at room temperature. The reaction was diluted with 30 ml. of methylene chloride, washed with 5% bicarbonate and two portions of 100 ml. of water. The organic layer was dried over magnesium sulfate, filtered and evaporated to dryness affording 546 mg. (100%) of 4 as yellow foam, which was pure enough for further reactions. An analytical specimen was obtained, by recrystallizing from methylene chloride and n-pentane, as white prisms, m.p. 132°-133° C.

Anal. Calc'd for $C_{30}H_{28}N_2O_6S$: C, 66.25; H, 5.15; N, 5.15. Found: C, 66.60; H, 5.30; N, 5.46.

ir (KBr) 1780, 1725 and 1675 cm⁻¹.

nmr (CDCl₃) δ2.1 (s. 3H), 3.45 (s.3H), 4.56 (s. 2H), 5.15 (d. J=5.0 Hz 1H), 5.90 (q, J=5.0, 12 Hz, 1H), 6.8-7.8 (m. 16H).

EXAMPLE 2

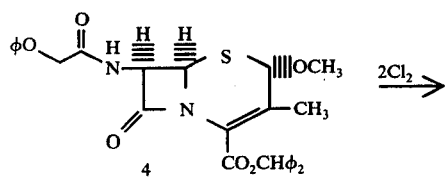

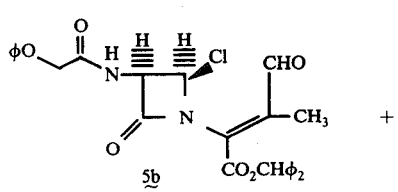

To a cooled (−20° C.) solution of 5.40 g. (10.0 mmole) of the 2-methoxycephem 4 in 80 ml. of dry methylene chloride was added dropwise a solution of 1.57 g. (22.0 mmole) of chlorine in 15 ml. of carbon tetrachloride over a 10 minute period and the slightly yellow solution was allowed to stir at −20° C. for 60 minutes under nitrogen. The reaction was poured into 120 ml. of ethyl acetate and shaken vigorously with 100 ml. of ice-cold water for 10 minutes. The organic layer was washed with brine, dried over magnesium sulfate, filtered and evaporated to dryness affording 5.9 g. (quantitative yield) of yellow oil which was a mixture of cis 5b and trans 5a (α-chloro/β-chloro = 1/9). This oily material was chromatographed over 200 g. of silica gel and elution with 10% ethyl acetate in methylene chloride giving 4.3 g. (75%) of a pure mixture of 5a and 5b as a white foam.

Anal. Calc'd for $C_{29}H_{25}N_2O_6Cl·H_2O$: C, 63.30; H, 4.92; N, 5.10; Cl, 6.45. Found: C, 63.84; H, 4.64; N, 5.31; Cl, 6.04.

ir (KBr) 1795,1730, 1685 and 1530 cm⁻¹.

nmr (CDCl₃) of 5b δ2.2 (s, 3H), 4.62 (s, 2H), 5.70 (q, J=4.2, 11.5 Hz, 1H), 6.3 (d, J=4.2 Hz, 1H), 6.8-7.5 (m) 10.0 (s, 1H).

nmr (CDCl₃) of 5a δ2.15 (s, 3H), 4.56 (s, 2H), 5.10 (q, J=1.2, 10 Hz, 1H), 6.20 (d, J=1.2 Hz, 1H), 6.8-7.5 (m) 9.95 (s, 1H).

EXAMPLE 3

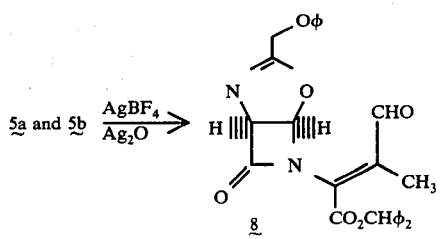

To a cooled (0° C.) solution of 1.13 g (2.0 mmole) of 5b and 5a (9:1) in 15 ml. of dry methylene chloride was added at once 487 mg. (2.5 mmole) of silver fluoroborate and 800 mg. (2.5 mmole) of silver oxide and stirred vigorously at 0° C. for 60 minutes under nitrogen. The reaction was filtered and the filtrate was treated with 10 ml. of brine. The mixture was filtered again through "Celite" under suction. The organic layer was dried over magnesium sulfate, filtered and condensed to 5 ml. of volume which was then poured into 150 ml. of n-pentane to give 895 mg. (85%) of 8 as a white powder.

Anal. Calc'd for $C_{29}H_{24}N_2O_6$: C, 70.15; H, 4.87; N, 5.31. Found: C, 69.29; H, 5.09; N, 5.75.

ir (KBr 1780, 1720 and 1680 cm⁻¹.

nmr (CDCl₃) δ2.15 (s, 3H), 4.75 (s, 2H), 5.40 (d, J=4.5Hz, 1H), 6.3 (d, J=4.5 Hz, 1H), 6.8-7.5 (m, 15H), 9.85 (s, 1H).

EXAMPLE 4

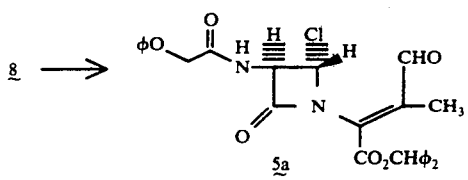

To a cooled (0° C.) solution of 2.11 g. (4.0 mmole) of 8 in 50 ml. of dry methylene chloride was bubbled HCl gas slowly for 2 minutes. No starting material was detected by tlc. The reaction was washed with ice-cold 5% bicarbonate and dried over magnesium sulfate. The dried solvent was evaporated to dryness affording 2.2 g. (almost quantitative yield) of 5a as a slightly yellow foam. Nmr of this material was identical with the minor component in the ring opening products of 2-methoxycephem 4 by chlorine.

EXAMPLE 5

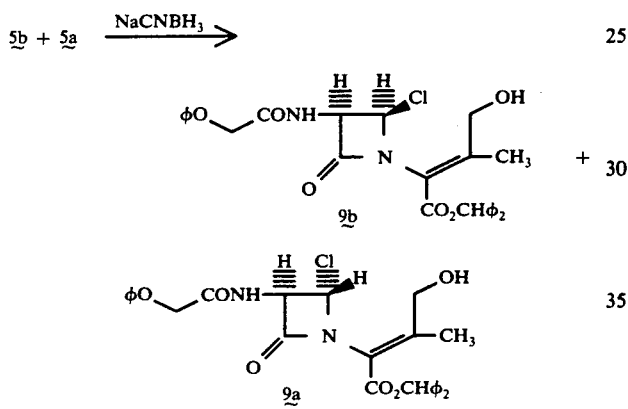

To a cooled (0° C.) solution of 564 mg. (1.0 mmole) of 5b and 5a (9:1) in 9 ml. of THF and 1 ml. of acetic acid was added 100 mg. (1.6 mmole) of sodium cyanoborhydride (NaCNBH$_3$) and the mixture was stirred at 0° C. for 30 minutes under nitrogen. The reaction was poured into ice cold 50 ml. of ethyl acetate —30 ml. of 5% bicarbonate solution. The organic layer was then washed with brine, dried over magnesium sulfate and filtered. The filtrate was evaporated to a colorless oil which gave 510 mg. (91%) of 9b and 9a (ca 9:1) as amorphous solids upon trituration with n-pentane-ether (5:1).

Anal. Calc'd for $C_{29}H_{27}N_2O_6Cl$: C, 65.01; H, 5.05; N, 5.23. Found: C, 64.67; H, 4.69; N, 5.69.

ir (KBr) 3400 (broad), 1785, 1730, 1690 and 1530 cm$^{-1}$.

nmr (CDCl$_3$) of 9b $\delta$2.35 (s, 3H), 4.2 (d, J=12Hz, 1H), 4.4 (d, J=12Hz, 1H), 4.51 (s, 2H), 5.6 (q, J=3.9, 9.5 Hz, 1H), 5.9 (d, J=3.9Hz, 1H), 6.7–7.5 (m, 15H).

nmr (CDCl$_3$) of 9a (only following peaks could be observed in the spectrum of 9b and 9a mixture. $\delta$2.34 (s), 5.0 (q, J=1.5, 10Hz), 5.8 (d, J=1.5Hz).

I claim:

1. A compound having the formula

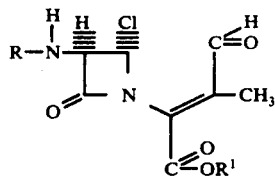

wherein R is an amine protecting group and R$^1$ is the residue of an ester group which can be removed readily.

2. The compound having the formula

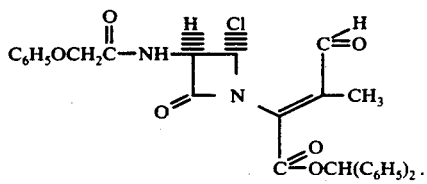

* * * * *